US011147663B2

United States Patent
Cumming

(10) Patent No.: US 11,147,663 B2
(45) Date of Patent: *Oct. 19, 2021

(54) INTRAOCULAR LENS

(71) Applicant: James Stuart Cumming, Laguna Beach, CA (US)

(72) Inventor: James Stuart Cumming, Laguna Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/082,960

(22) Filed: Mar. 28, 2016

(65) Prior Publication Data

US 2016/0206421 A1 Jul. 21, 2016

Related U.S. Application Data

(63) Continuation of application No. 13/910,076, filed on Jun. 4, 2013, now Pat. No. 9,295,544.

(60) Provisional application No. 61/689,394, filed on Jun. 5, 2012.

(51) Int. Cl.
*A61F 2/16* (2006.01)

(52) U.S. Cl.
CPC .......... *A61F 2/1629* (2013.01); *A61F 2/1613* (2013.01); *A61F 2/1624* (2013.01); *A61F 2002/1681* (2013.01); *A61F 2002/1682* (2015.04); *A61F 2002/1689* (2013.01)

(58) Field of Classification Search
CPC .... A61F 2/1613; A61F 2/1624; A61F 2/1629; A61F 2/1635; A61F 2/1637; A61F 2/1648; A61F 2002/1681; A61F 2002/1689; A61F 2002/1682
See application file for complete search history.

(56) References Cited

U.S. PATENT DOCUMENTS

| | | |
|---|---|---|
| 2,834,023 A | 5/1958 | Wolfgang |
| 4,073,014 A | 2/1978 | Poler |
| 4,118,808 A | 10/1978 | Poler |
| 4,122,556 A | 10/1978 | Poler |
| 4,159,546 A | 7/1979 | Shearing |
| 4,168,547 A | 9/1979 | Konstantinov et al. |
| 4,173,798 A | 11/1979 | Welsh |
| 4,174,543 A | 11/1979 | Kelman |
| 4,206,518 A | 6/1980 | Jardon et al. |
| 4,244,060 A | 1/1981 | Hoffer |
| 4,254,509 A | 3/1981 | Tennant |
| 4,277,851 A | 7/1981 | Choyce et al. |
| 4,298,995 A | 11/1981 | Poler |
| 4,304,012 A | 12/1981 | Richard |
| 4,409,690 A | 10/1983 | Gess |

(Continued)

FOREIGN PATENT DOCUMENTS

| | | |
|---|---|---|
| CA | 2110184 A1 | 12/1992 |
| CH | 681687 | 5/1993 |

(Continued)

OTHER PUBLICATIONS

Dykstra, M., et al. Biological Electron Microscopy: Theory, Techniques, and Troubleshooting, 2003, p. 81.

(Continued)

*Primary Examiner* — William H Matthews
(74) *Attorney, Agent, or Firm* — Sheppard, Mullin, Richter & Hampton LLP

(57) ABSTRACT

An intraocular lens comprising a lens optic coupled to at least one haptic and at least one deformable connecting bar positioned between the lens optic and the at least one haptic.

17 Claims, 1 Drawing Sheet

(56) References Cited

U.S. PATENT DOCUMENTS

| | | |
|---|---|---|
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,629,462 A | 12/1986 | Feaster |
| 4,648,878 A | 3/1987 | Kelman |
| 4,664,665 A | 5/1987 | Reuss et al. |
| 4,664,666 A | 5/1987 | Barrett |
| 4,673,406 A | 6/1987 | Schlegel |
| 4,681,102 A | 7/1987 | Bartell |
| 4,704,123 A | 11/1987 | Smith |
| 4,710,195 A | 12/1987 | Glovinazzo |
| 4,718,904 A | 1/1988 | Thornton |
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,769,033 A | 9/1988 | Nordan |
| 4,769,035 A | 9/1988 | Kelman |
| 4,772,283 A | 9/1988 | White |
| 4,778,463 A | 10/1988 | Hetland |
| 4,781,719 A | 11/1988 | Kelman |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,599 A | 6/1989 | Bronstein |
| 4,842,601 A | 6/1989 | Smith |
| 4,846,833 A | 7/1989 | Cumming |
| 4,862,885 A | 9/1989 | Cumming |
| 4,865,601 A | 9/1989 | Caldwell et al. |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,089,022 A | 2/1992 | Koester et al. |
| 5,139,518 A | 8/1992 | White |
| 5,141,507 A | 8/1992 | Paraekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,489,302 A | 2/1996 | Skottun |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,647,865 A | 7/1997 | Swinger |
| 5,674,282 A | 10/1997 | Cumming |
| 5,686,414 A | 11/1997 | Scannon |
| 5,699,142 A | 12/1997 | Lee et al. |
| 5,716,403 A | 2/1998 | Tran et al. |
| 5,800,532 A | 9/1998 | Lieberman |
| 5,837,156 A | 11/1998 | Cumming |
| 5,843,187 A | 12/1998 | Bayers |
| 5,873,879 A | 2/1999 | Figueroa et al. |
| 5,919,230 A | 7/1999 | Sambursky |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,161,544 A | 12/2000 | DeVore |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 | 3/2001 | Cumming |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |
| 6,503,275 B1 | 1/2003 | Cumming |
| 6,503,276 B2 | 1/2003 | Lang et al. |
| 6,517,577 B1 | 2/2003 | Callahan et al. |
| 6,524,340 B2 | 2/2003 | Isreal |
| 6,540,353 B1 | 4/2003 | Dunn |
| 6,558,420 B2 | 5/2003 | Green |
| 6,613,343 B2 | 9/2003 | Dillingham et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Landreville et al. |
| 6,695,881 B2 | 2/2004 | Peng et al. |
| 6,749,634 B2 | 6/2004 | Hanna |
| 6,767,363 B1 | 7/2004 | Bandhauer et al. |
| 6,849,091 B1 | 2/2005 | Cumming |
| 6,858,040 B2 | 2/2005 | Nguyen et al. |
| 6,881,225 B2 | 4/2005 | Okada |
| 6,884,263 B2 | 4/2005 | Valyunin |

(56) References Cited

U.S. PATENT DOCUMENTS

| | | |
|---|---|---|
| 6,921,416 B2 | 7/2005 | Khoury |
| 6,926,736 B2 | 8/2005 | Peng |
| 6,932,839 B1 | 8/2005 | Kamerling et al. |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,388,608 B1 | 3/2013 | Kaluzna |
| 8,523,942 B2 | 9/2013 | Cumming |
| 8,734,512 B2 | 5/2014 | Cumming |
| 8,764,823 B2 | 7/2014 | Cumming |
| 9,034,036 B2 | 5/2015 | Cumming |
| 2001/0001836 A1 | 5/2001 | Cumming |
| 2002/0120329 A1 | 8/2002 | Lang et al. |
| 2002/0138140 A1 | 9/2002 | Hanna |
| 2003/0060881 A1 | 3/2003 | Glick et al. |
| 2003/0078658 A1 | 4/2003 | Zadno-Azizi |
| 2003/0097177 A1 | 5/2003 | Tran |
| 2003/0109925 A1 | 6/2003 | Ghazizadeh et al. |
| 2003/0135272 A1 | 7/2003 | Brady et al. |
| 2003/0142269 A1 | 7/2003 | Cumming |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0215207 A1 | 10/2004 | Cumming |
| 2004/0220666 A1 | 11/2004 | Cumming |
| 2004/0243232 A1 | 12/2004 | Cumming |
| 2004/0249456 A1 | 12/2004 | Cumming |
| 2005/0021140 A1 | 1/2005 | Liao |
| 2005/0027354 A1 | 2/2005 | Brady et al. |
| 2005/0075732 A1 | 4/2005 | Israel |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064077 A1 | 3/2006 | Peyman |
| 2006/0064162 A1 | 3/2006 | Klima |
| 2006/0100704 A1 | 5/2006 | Blake et al. |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0021832 A1 | 1/2007 | Nordan |
| 2007/0032867 A1 | 2/2007 | Cumming |
| 2007/0129800 A1 | 6/2007 | Cumming |
| 2007/0129803 A1 | 6/2007 | Cumming et al. |
| 2007/0135915 A1 | 6/2007 | Klima |
| 2007/0142908 A1 | 6/2007 | Xu |
| 2007/0198084 A1 | 8/2007 | Cumming |
| 2007/0244472 A1 | 10/2007 | Kuhn et al. |
| 2008/0027538 A1 | 1/2008 | Cumming |
| 2008/0027539 A1 | 1/2008 | Cumming |
| 2008/0027540 A1 | 1/2008 | Cumming |
| 2008/0046077 A1 | 2/2008 | Cumming |
| 2008/0086208 A1 | 4/2008 | Nordan |
| 2008/0154362 A1 | 6/2008 | Cumming |
| 2008/0281415 A1 | 11/2008 | Cumming |
| 2008/0281416 A1 | 11/2008 | Cumming |
| 2008/0288066 A1 | 11/2008 | Cumming |
| 2008/0294254 A1 | 11/2008 | Cumming et al. |
| 2008/0319545 A1 | 12/2008 | Cumming |
| 2009/0005866 A1 | 1/2009 | Cumming |
| 2009/0234449 A1 | 9/2009 | De Juan, Jr. et al. |
| 2009/0248154 A1 | 10/2009 | Dell |
| 2010/0004742 A1 | 1/2010 | Cumming |
| 2010/0057202 A1 | 3/2010 | Bogaert |
| 2011/0313519 A1 | 12/2011 | Cumming |
| 2011/0313524 A1 | 12/2011 | Cumming |
| 2011/0313525 A1 | 12/2011 | Cumming |
| 2011/0313526 A1 | 12/2011 | Cumming |
| 2012/0296424 A1 | 11/2012 | Betser |
| 2013/0073039 A1 | 3/2013 | Mirlay |
| 2013/0231742 A1 | 9/2013 | Deacon et al. |
| 2014/0094909 A1 | 4/2014 | Cumming |
| 2014/0155871 A1 | 6/2014 | Cumming |
| 2014/0172093 A1 | 6/2014 | Cumming |
| 2015/0012088 A1 | 1/2015 | Cumming |
| 2015/0073550 A1 | 3/2015 | Cumming |
| 2015/0088254 A1 | 3/2015 | Cumming |
| 2015/0182327 A1 | 7/2015 | Cumming |
| 2015/0182328 A1 | 7/2015 | Cumming |
| 2015/0245904 A1 | 9/2015 | Cumming |
| 2015/0245905 A1 | 9/2015 | Cumming |

FOREIGN PATENT DOCUMENTS

| | | |
|---|---|---|
| DE | 3626869 | 2/1988 |
| FR | 2728458 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |
| WO | WO 2007/037180 | 4/2007 |
| WO | WO 2009/048656 | 4/2009 |
| WO | WO 2009/086511 | 7/2009 |
| WO | WO 2011/151839 | 12/2011 |

OTHER PUBLICATIONS

International Search Report and Written Opinion for PCT/US13/61452 dated Feb. 24, 2014 in 11 pages.

Davison, J.A., Chapter 11: Intraocular Lenses, Duane's Clinical Ophthalmology on CD-ROM, Lippincott Wllliams & Wilkins, 2005, vol. 6, pp. 1-46.

International Search Report and Written Opinion for PCT/US2014/072518 dated Jul. 23, 2015 in 15 pages.

Internet Archive Wayback Machine; Crystalens—Is Crystalens right for you?; downloaded from http://web.archive.org/web/20141025080709/http://crystalens.com/en-US/iscrystalensrightforyou.aspx (Archived Oct. 25, 2014; printed on Aug. 12, 2015).

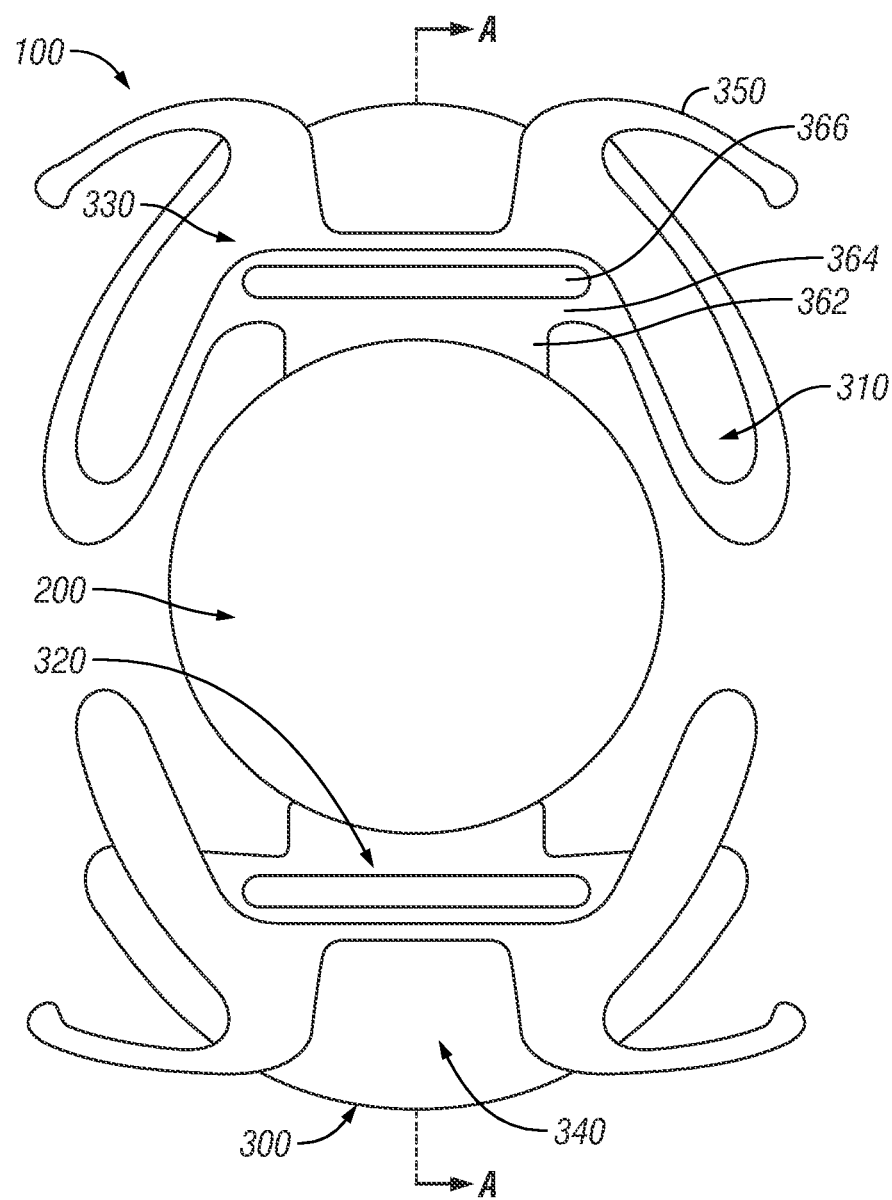

INTRAOCULAR LENS

CROSS-REFERENCE TO RELATED APPLICATIONS

This application is a continuation of U.S. patent application Ser. No. 13/910,076, filed on Jun. 4, 2013, now U.S. Pat. No. 9,295,544, which claims the benefit of U.S. Provisional Application Ser. No. 61/689,394, filed on Jun. 5, 2012, the contents of which are all hereby incorporated by reference herein in their entirety. This application is also related to U.S. application Ser. No. 13/017,189, filed on Jan. 31, 2011, Ser. No. 13/092,359, filed on Apr. 22, 2011, Ser. No. 13/111,599, filed on May 19, 2011, Ser. No. 13/155,327, filed on Jun. 7, 2011, Ser. No. 13/472,354, filed on May 15, 2012, Ser. No. 13/472,893, filed on May 16, 2012, and Ser. No. 13/891,086, filed on May 9, 2013, the contents of which are hereby incorporated by reference herein in their entireties.

BACKGROUND

Premium intraocular lenses (IOLs) implanted during cataract surgery are categorized three ways: accommodating, multifocal, and toric intraocular lenses.

The best visual acuity is achieved with the single focus accommodating lenses. The optic of these lenses moves forward and backward upon constriction and relaxation of the ciliary muscle. However, for reading in dim lighting conditions, or for small print, weak reading glasses are often necessary.

The multifocal lenses focus light on the retina at either two or three focal lengths. Thus, there is more than one image on the retina simultaneously. This creates problems since the amount of light in focus is divided between the multiple focal points, and contrast sensitivity is thereby reduced, making vision at all distances difficult in dim lighting. In addition, there are severe problems when driving at night when the pupil is dilated. Many patients experience severe glare and halos and many have had to have the multifocal lenses explanted and replaced with a single vision standard lens, because of this problem. However, the near vision with the multifocal lenses is superior to that of the current accommodating lens.

The toric lenses correct the eyes that have significant astigmatism.

The currently marketed plate accommodating intraocular lenses provide excellent distance and intermediate vision but sometimes require weak, +1.00, reading glasses for prolonged reading, for seeing small print, or reading in dim lighting conditions.

Furthermore, it is important for intraocular lenses to have a consistent location along the axis of the eye to provide good uncorrected distance vision and to center in the middle of the vertical meridian of the eye. Without excellent uncorrected distance vision there is no point in implanting lenses designed to give seamless vision from far to near.

The original intraocular lens consisted of a single optic. These lenses frequently de-centered and dislocated and it was discovered that there was a need to center and fixate the lens optic in the vertical meridian of the eye.

Attachments to the optic that center and fixate the lens within the capsular bag are called haptics. Traditionally, haptics consist of multiple flexible loops of various designs, J loops, C loops, closed loops, and flexible radial arms. Recently, traditional haptics have been replaced in some lens designs with oblong, flat flexible plates, called plate haptics. These plate haptics usually made from silicone, are solid, flat, flexible and between 3.0 and 6.0 mm in width, 0.20 to 0.75 mm thick, and may have tapered, rounded or parallel sides. Plate haptics often have flexible loops or fingers that help center and fixate the lens within the capsular bag. These flexible fingers extend beyond the distal or outer end of the plate haptics and slightly beyond the diameter of the capsular bag and are designed to flex centrally to center and fixate the lens and its optic within the capsular bag.

An intraocular lens (IOL) is a lens implanted into the eye, usually replacing a normal human lens that has been clouded over by a cataract, or can replace a normal human lens as a form of refractive surgery to change the eye's optical power.

An accommodating IOL (AIOL) permits refocusing of the eye by means of movement along the optical axis in response to the constriction or relaxation of ciliary muscles. Near vision results from a forward movement of the optic upon constriction of the ciliary muscle which increases the pressure in the posterior part of the eye with a simultaneous decrease in pressure in the anterior part of the eye. Distance vision results from the reverse pressure change that takes place upon relaxation of the ciliary muscle and the resultant backwards movement of the lens. The movement of the optic enables the patient implanted with the lens to automatically change their vision between far, intermediate and near.

AIOLs are known to consist of opposing haptics positioned on either side of a lens optic. Once a patient's cataract is removed, e.g. by phacoemulsification, the AIOL is placed into the empty capsular bag. The haptics help to center the AIOL and fixate it within the capsular bag by fibrosis. Such AIOLs are described in U.S. Pat. Nos. 5,674,282, 5,476,514, and 5,496,366, to Cumming, herein incorporated by reference in its entirety.

And although current AIOLs provide patients with significantly restored distance and intermediate vision, adequate near vision is commonly lacking—often requiring that patients use weak reading glasses to enhance near vision. Multi-focal and toric lens solutions suffer from the disadvantages identified above.

SUMMARY OF THE INVENTION

An intraocular lens according to an embodiment of the present invention is described that overcomes the deficiencies of present designs noted above.

The field of the invention is an intraocular lens that provides seamless vision from distance to near.

An intraocular lens is provided comprising a lens optic coupled to at least one haptic and a torsion bar positioned between the lens optic and the at least one haptic.

The intraocular lens may comprise, for example, an intraocular lens for improving vision wherein the intraocular lens is configured for implantation in a capsular bag of a patient. The lens comprises: a single focus, biconvex optic and a pair of plate haptics.

The single focus, biconvex optic comprises an optical material. The optic has a circular configuration configured to be centered about an optical axis of the eye when implanted. The lens has a longitudinal axis defining a length dimension of the lens and a transverse axis defining a width dimension of the lens, both of which are orthogonal to the optical axis of the eye when implanted. The transverse axis of the lens is perpendicular to the longitudinal axis of the lens. The optic has a first side and a second side. The first side of the optic and the second side of the optic are on opposite sides of the transverse axis of the lens.

One of the plate haptics is coupled to the first side of the optic, and the other plate haptic is coupled to the second side of the optic. The longitudinal axis of the lens extends through the optic and the pair of haptics. Each plate haptic comprises a proximal end and a distal end, a frame, and a pair of opposing lateral paddles. The proximal end is closer to the optic than the distal end. Each plate haptic comprises a haptic material. The frame is embedded within the haptic material. The frame comprises a different material that is more rigid than the haptic material to provide longitudinal rigidity to the haptic. The pair of opposing lateral paddles are configured to stabilize the lens to prevent the intraocular lens from tilting. The pair of lateral paddles form bilateral extensions of the haptic to at least partially surround the optic. The pair of lateral paddles are configured to locate the optic in a posterior position along the optical axis of the eye when implanted. The more rigid material of the frame extends into each lateral paddle to provide longitudinal rigidity to the pair of lateral paddles and the plate haptic. The haptics are configured to vault posteriorly in response to an end-to-end compressive force from the capsular bag such that the paddles are posterior to the distal ends of the haptics, the paddles being configured to apply force on the vitreous cavity. Each plate haptic is flexibly coupled to the optic by a haptic coupling system. The haptic coupling system comprises a strap, a transverse slot, and a connecting bar. The strap is coupled to the optic. An elongate axis of the strap is substantially perpendicular to the longitudinal axis of the lens. A length of the strap is measured along the elongate axis of the strap. The transverse slot extends completely through the haptic coupling system. The transverse slot is distal to the strap. An elongate axis of the slot is substantially perpendicular to the longitudinal axis of the lens. A length of the slot measured along its elongate axis is between 2.0 mm and 5.0 mm. The connecting bar is distal to the strap and proximal to the elongate slot such that the connecting bar is between the strap and the elongate slot. The longitudinal axis of the lens extends through the strap, the connecting bar, and the slot. The connecting bar extends laterally from one of the lateral paddles to the other of the lateral paddles. Each of the connecting bars is configured to stretch and twist upon the end-to-end compressive force from the capsular bag to position the optic posteriorly in the capsular bag upon implantation.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE FIGURES

Illustrated in the accompanying drawing(s) is at least one of the best mode embodiments of the present invention In such drawing(s):

FIG. 1 illustrates a top plan view of an AIOL according to at least one embodiment of the present invention.

DETAILED DESCRIPTION OF THE PREFERRED EMBODIMENTS

The above-described drawing FIGURES illustrate the described invention in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present invention.

A preferred embodiment will now be described with reference to FIG. 1.

An accommodating intraocular lens (AIOL) 100 comprises: an optic 200 coupled to at least one haptic 300.

The AIOL 100 is placed into the capsular bag of a patient's eye after cataract surgery via known techniques such as, for example, phacoemulsification. The lens is centered so that the optical axis of the lens coincides with that of the patient's eye. The haptics 300 contact the capsular bag and the natural fibrosis of the tissue secures the haptics 300, and consequently the AIOL 100, in place.

The optic 200 is preferably a single focus optic that gathers the incoming light and focuses it on the retina of the patient so as to effect vision. The optic 200 may be biconvex, refractive, diffractive, plano-convex, Fresnell, spheric, aspheric, toric, or of any other type that is substantially single focus. In order to permit the optic 200 to be inserted into the eye through a small incision, the optic 200 is preferably made of a flexible optical material, such as, for example, silicone, acrylic, hydrogel, or other flexible optical material now known or hereafter developed.

The at least one haptic 300 comprises a proximal end 320 opposite a distal end 340. The proximal end 320 is flexibly coupled to a periphery of the optic 200. In at least one embodiment, the AIOL 100 comprises opposing haptics positioned linearly along a longitudinal axis A of the AIOL 100.

The haptic body may be substantially flexible in the transverse direction and substantially rigid in the longitudinal direction so as to enable the AIOL 100 to be folded and inserted into the eye via a small incision. One of ordinary skill will appreciate that while substantial rigidity may promote vaulting; the degree of rigidity imposed is not intended to preclude an effective vault of the optic. It is preferable that the haptic be constructed of the same or similar flexible material as the optic, including, but not limited to: silicone, hydrogel, acrylic, or similar material.

The plate haptic 300 may comprise opposing lateral paddles 310, the haptic and paddles operable to engage, fixate and center the haptic into the capsular bag. Such exemplary haptics and paddles are discussed in U.S. patent Ser. Nos. 13/017,189; 13/092,359; 13/111,599; 13/155,327; 13/472,893; and Ser. No. 13/472,354, incorporated herein by reference in their entireties.

A frame 330 may be embedded within the haptic 300 so as to promote the longitudinal rigidity thereof. The frame may be formed of polyimide, prolene, polymethylmethanylate (PMMA), titanium, or similar material. The frame may be a meshwork of rigid material molded into flexible material and/or a lattice of such material. Such exemplary frames are discussed in U.S. patent Ser. Nos. 13/017,189; 13/092,359; 13/111,599; 13/155,327; 13/472,893; and Ser. No. 13/472,354, incorporated herein by reference in their entireties.

The haptic 300 may further comprise projections 350, or fingers, extending from the distal end to engage the capsular bag and secure and center the AIOL thereto. The projections may be homogeneous with the frame and may be made of either polyimide, PMMA, acrylic or any other inert material. Such exemplary projections are discussed in U.S. patent Ser.

Nos. 13/017,189; 13/092,359; 13/111,599; 13/155,327; 13/472,893; and Ser. No. 13/472,354, incorporated herein by reference in their entireties.

The proximal end 320 of the haptic 300 may be coupled to the optic via connecting portion 360 that operates to permit contraction of the ciliary muscles to cause an end-to-end compression of opposing haptics with an increase in vitreous pressure, thus moving the optic substantially forward. The connecting portion 360 preferably comprises a strap 362 adjacent the optic periphery and flexibly coupled thereto, a torsion bar opposite the strap. Accordingly, the strap, torsion bar and slot are arranged linearly along the longitudinal axis of the AIOL.

The strap 362 couples the optic to the haptic and is preferably of the same material as the haptic. The strap assists in accommodation in that they decrease the resistance to the pressure that pushes the optic forward. Exemplary straps are described in U.S. patent Ser. Nos. 13/017,189; 13/092,359; 13/111,599; and Ser. No. 13/155,327; 13/472,893; and Ser. No. 13/472,354, incorporated herein by reference in their entireties.

The torsion bar 364 extends laterally between opposing paddles of the haptic. Moreover, the torsion bar is preferably integral to the haptic at each of the lateral ends (with respect to the longitudinal axis A) of the torsion bar, and is preferably of the same flexible material as the haptic. However, the torsion bar may also be of a different material than the haptic such that the torsion bar is substantially more rigid or more flexible than the haptic. As mentioned above, the torsion bar is adjacent the strap at one longitudinal end (with respect to the longitudinal axis A), and adjacent the elongate slot. In at least one embodiment, the torsion bar may be from 0.1 to 2.0 mm in length. Preferably, the torsion bar has a circular cross-section, but all cross-sectional shapes are specifically contemplated.

The elongate slot 366 is an aperture formed in the haptic that extends laterally and parallel to the torsion bar and partially separating the torsion bar from the balance of the haptic. Preferably, the slot comprises an oval shape, but all shapes are specifically contemplated. As mentioned above, the slot is adjacent the torsion bar distal to the optic. Preferably, the slot dimensions ranging from 0.1 to 0.5 mm in height and 2.0 to 5.0 mm in length.

On insertion into the eye, the haptics are vaulted posteriorly. The haptics move centrally and posteriorly in response to ciliary muscle contraction, i.e. end-to-end compression. Such movement, combined with the change in vitreous pressure, causes the optic to vault anteriorly and the haptics to vault centrally and posteriorly to further increase the pressure in the posterior vitreous cavity of the eye. This increase in pressure is further facilitated by the paddles dipping posteriorly into the vitreous cavity, thereby causing the optic to move forward. This effect is further facilitated by the stretching and/or rotation of the torsion bars in response to the movement. Relaxation of the ciliary muscle causes an increase in the diameter of the ciliary muscle and a reduction in vitreous cavity pressure with an increase in pressure in the anterior part of the eye such that the optic 200 moves posteriorly to the distant vision position.

In at least one embodiment, the longitudinal length of the AIOL (i.e., from distal end to distal end) may be between approximately 9.0-11.0 mm, with the diameter as measured from the tips of the lateral projections being between approximately 11.5-12.0 mm. The haptics are preferably between 3.0-6.0 mm wide and 0.20-0.75 mm thick, while the optic may be approximately 5.0 mm.

The enablements described in detail above are considered novel over the prior art of record and are considered critical to the operation of at least one aspect of the invention and to the achievement of the above-described objectives. The words used in this specification to describe the instant embodiments are to be understood not only in the sense of their commonly defined meanings, but to include by special definition in this specification: structure, material, or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense, it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that the named inventor believes that the claimed subject matter is what is intended to be patented.

The invention claimed is:

1. An intraocular lens configured for implantation in the capsular bag of an eye of a patient, the intraocular lens comprising:
    at least one haptic;
    a lens optic coupled to the at least one haptic;
    an elongate slot partially traversing the at least one haptic in a lateral direction; and
    a torsion bar positioned between the lens optic and the elongate slot such that the torsion bar can rotate to position the lens optic in a posterior location along the axis of the eye;
    wherein the at least one haptic is coupled to the lens optic via a strap positioned adjacent to a periphery of the lens optic and flexibly coupled thereto;
    wherein the torsion bar is positioned adjacent to the strap on an opposite side of the strap from the lens optic;
    wherein the elongate slot is adjacent to the torsion bar on an opposite side of the torsion bar from the strap; and
    wherein the elongate slot is configured as an aperture extending completely through the at least one haptic, from front to back.

2. The intraocular lens of claim 1, wherein the torsion bar is between 0.1 and 2.0 mm in length.

3. The intraocular lens of claim 1, wherein the torsion bar is of the same material as the at least one haptic.

4. The intraocular lens of claim 1, wherein the elongate slot is 0.1 to 0.5 mm in height and 2 to 5 mm in length.

5. The intraocular lens of claim 1, wherein said at least one haptic is substantially rigid in a longitudinal direction.

6. The intraocular lens of claim 5, wherein said at least one haptic is at least one plate haptic.

7. The intraocular lens of claim 5, wherein said at least one haptic comprises a pair of lateral paddles which partially surround said lens optic.

8. The intraocular lens of claim 7, wherein:
the at least one haptic comprises a frame; and
the frame extends into said pair of lateral paddles to provide longitudinal rigidity to the pair of lateral paddles.

9. The intraocular lens of claim 1, wherein:
said at least one haptic comprises a frame which is longitudinally substantially rigid; and
said at least one haptic is substantially flexible in a transverse direction to enable the intraocular lens to be folded for insertion through a small incision in the eye.

10. The intraocular lens of claim 1, wherein the torsion bar has a lateral extent that is greater than a lateral extent of the strap.

11. The intraocular lens of claim 1, wherein the strap, the torsion bar, and the slot are arranged linearly along a longitudinal axis of the intraocular lens.

12. The intraocular lens of claim 1, wherein the torsion bar and the slot extend laterally and parallel to each other.

13. The intraocular lens of claim 1, wherein:
the at least one haptic comprises a pair of opposing lateral paddles; and
the torsion bar extends laterally between the pair of opposing lateral paddles.

14. The intraocular lens of claim 13, wherein the torsion bar extends along a lateral axis perpendicular to a longitudinal axis of the intraocular lens.

15. The intraocular lens of claim 14, wherein the lateral axis of the torsion bar extends through each of the pair of opposing lateral paddles.

16. The intraocular lens of claim 13, wherein the torsion bar extends laterally from one of the pair of opposing lateral paddles to the other of the pair of opposing lateral paddles.

17. The intraocular lens of claim 1, wherein the torsion bar has a circular cross-section.

\* \* \* \* \*